US009566389B2

(12) United States Patent
Hirschel et al.

(10) Patent No.: US 9,566,389 B2
(45) Date of Patent: Feb. 14, 2017

(54) INJECTION DEVICE WITH A COUPLING (71) Applicant: TECPHARMA LICENSING AG, Burgdorf (CH)

(72) Inventors: Jürg Hirschel, Bern (CH); Ursina Streit, Schönbühl (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 14/422,037

(22) PCT Filed: Jul. 17, 2013

(86) PCT No.: PCT/CH2013/000131
§ 371 (c)(1),
(2) Date: Jun. 12, 2015

(87) PCT Pub. No.: WO2014/019097
PCT Pub. Date: Feb. 6, 2014

(65) Prior Publication Data
US 2015/0283326 A1    Oct. 8, 2015

(30) Foreign Application Priority Data

Aug. 1, 2012  (EP) ..................... 12178915

(51) Int. Cl.
*A61M 5/315* (2006.01)
*A61M 5/20* (2006.01)
(52) U.S. Cl.
CPC .......... *A61M 5/31541* (2013.01); *A61M 5/20* (2013.01); *A61M 5/31553* (2013.01); *A61M 5/31583* (2013.01)
(58) Field of Classification Search
CPC ..................... A61M 5/31583; A61M 5/31553; A61M 5/31541
See application file for complete search history.

(56) References Cited

U.S. PATENT DOCUMENTS

2008/0147005 A1   6/2008  Moller et al.
2011/0054412 A1   3/2011  Eich et al.
(Continued)

FOREIGN PATENT DOCUMENTS

WO   WO 2006/045526    5/2006
WO   WO 2009/105909    9/2009
WO   WO 2011/101349    8/2011

*Primary Examiner* — Nathan R Price
*Assistant Examiner* — Melissa A Snyder
(74) *Attorney, Agent, or Firm* — Dorsey & Whitney LLP; Stuart R. Hemphill, Esq.

(57) ABSTRACT

The invention describes a locking arrangement which is advantageously used in an injection device for administering a medicinal drug, such as insulin for example. The locking arrangement has the following features: —a sleeve (15) having toothing (15c) along the inner circumference; —a sleeve-shaped, particularly a one-piece, coupling element (16) with a longitudinal axis (L), which is surrounded along its circumference by the sleeve (15), and which has a first section (16c) and a second section (16d), the first section (16c) being connected to the second section (16d) via an elastically deformable intermediate section (16e), the intermediate section (16e) having an engagement element (16f) which engages in the toothing (15c) of the sleeve (15); —a torque application device (11), particularly a torsion spring or a discharge spring, which applies a torque directed in a first rotational direction to the first section (16c) of the coupling element (16) around the longitudinal axis (L), wherein the engagement element (16f) is pushed into the toothing (15c) via the torque in such a manner that a rotation of the coupling element (16) relative to the sleeve (15) is blocked in the first rotational direction, wherein the second section (16d) of the coupling element (16) can be twisted relative to the first section (16c) around the longitudinal axis (L) in the first rotational direction, as a result of which the engagement of the engagement element (16f) in the toothing (Continued)

(15*c*), which blocks rotation in the first rotational direction, can be released in such a manner that a rotation of the coupling element (16) relative to the sleeve (15) in the first rotational direction is enabled.

20 Claims, 8 Drawing Sheets

(56) References Cited

U.S. PATENT DOCUMENTS

| | | | |
|---|---|---|---|
| 2012/0165752 A1* | 6/2012 | Holmqvist | A61M 5/31553 604/211 |
| 2013/0096513 A1 | 4/2013 | Smith | |

\* cited by examiner

INJECTION DEVICE WITH A COUPLING

The invention in general concerns a locking arrangement, in particular for a drive and/or metering unit of or for an injection device for administration of a liquid product, in particular a medication, for example insulin for diabetes treatment. The locking arrangement serves to prevent a torque, acting on a first rotational member in a first rotational direction on the drive side of the locking arrangement, from rotating a second rotational member disposed on the drive side of the locking arrangement and/or the first rotational member in the direction in which the drive-side torque acts. The locking arrangement additionally allows the second rotational member to rotate in the rotational direction in which the drive-side torque acts, so that the drive-side torque can rotate the first rotational member in the first rotational direction. The locking arrangement moreover allows the second rotational member to rotate the first rotational member in a second rotational direction, which is opposite to the torque exerted by the torque application device.

An injection device that has a torsion spring serving as drive spring, which is tensioned by rotation of a metering knob in a direction of rotation and can be slackened by rotation of the metering knob in the opposite direction is known from WO 2009/105909 A1. The injection device has a friction coupling, which keeps the tensioned spring from turning the metering knob backward. The parts required for this function are relatively expensive. The indicated device is a reusable device, and an emptied product container can be exchanged for a full one. However, since an injection device that can be discarded together with the product container as a single unit after the product container has been emptied (single-use injection device) is advantageous for many therapies, it is desirable for the injection device to be made as cheaply as possible.

It is a task of the invention to specify a locking arrangement, in particular for an injection device or a drive and metering device for an injection device, where the locking arrangement on the one hand should perform the desired function and on the other hand can be made cheaply.

The task is solved with the object of claim 1. Advantageous further developments follow from the dependent claims, the description, and the figures.

The invention starts from a locking arrangement that is disposed between a second, in particular input-side, rotational member, for example a winding member, and a first, in particular output-side, rotational member, for example a coupling member. The locking arrangement causes the first rotational member to be locked against rotation in the first rotational direction, in which the torque acting on the first rotational member acts when the second rotational member is unloaded, i.e., is free of external torques. By applying a torque to the second rotational member, the locking of the first rotational member in the first rotational direction is released, so that the first rotational member and the second rotational member can be rotated in the first direction. By applying a torque in the second rotational direction, which is opposite the first directional rotation, to the second rotational member, the first rotational member is rotated with the second rotational member.

The locking arrangement has a coupling element, in particular one-piece coupling element, which is disposed between the first rotational element and the second rotational member. Preferably, the first rotational member is connected rotation-fast to the coupling element and the second rotational member is likewise connected rotation-fast with the coupling element, in particular fastened or formed thereon.

The lock, which prevents the rotation of the first rotational member in the first rotational direction when the second rotational member is unloaded, is released by the coupling element becoming elastically deformed, in particular elastically twisted. In particular, the second rotational member can be twisted over the elastic coupling element relative to the first rotational member, in particular by an angle of less than 30°, in particular less than 10°.

The locking arrangement preferably comprises a sleeve, which has gear teeth over its inner circumference and which surrounds the twistable coupling element. The twistable coupling element has an engagement member, which engages the gear teeth in the inner circumference and disengages from the gear teeth through the twisting of the coupling element. The sleeve can, for example, be a housing or an intermediate sleeve, which is disposed between the housing and the coupling element and which is rotatable, for example, relative to the housing.

The sleeve-shaped, in particular one-piece, coupling element has a first, in particular ring-shaped, section and a second, in particular ring-shaped, section. The first section is connected to the second section via at least one elastically deformable intermediate section, for example via two intermediate sections, which, for example, are uniformly distributed over the circumference of the coupling element. The intermediate section has the engagement member, which engages in the gear teeth of the sleeve.

The locking arrangement comprises a torque application device, which loads, in particular permanently so, the first section of the coupling element and/or the first rotational member with a torque directed in the first rotational direction about the lengthwise axis. The torque application device can be, for example, a spring, for example a torsion spring. A torsion spring can, for example, be a coil spring or a helical spring. The torque application device can, for example, act on the rotational member, which is connected to the first section, in particular separably connected, or which is formed on the first section. The engagement member of the coupling element is pressed by said torque into the gear teeth of the sleeve. The intermediate section is in particular designed so that the engagement member is pressed into the gear teeth. Through this, a rotation of the coupling element is blocked relative to the sleeve in the first rotational direction, namely in the direction in which the torque of the torque application device acts.

The second section of the coupling element can be twisted relative to the first section in the first rotational direction about the lengthwise axis. In doing so, the at least one intermediate section becomes elastically deformed. The engagement of the engagement member in the gear teeth, which blocks rotation in the first rotational direction, is released by torsion, or twisting, of the second section relative to the first section, or the deformation of the at least one intermediate section. In this way, a rotation of the coupling element relative to the sleeve in the first rotational direction, in particular at least by one angular increment, is enabled.

The internal gear teeth of the sleeve have a plurality of teeth distributed over the inner circumference, in particular uniformly distributed. The angular spacing between two adjacent teeth can be called one angular increment. The coupling element can be rotated relative to the sleeve in the first rotational direction at least or preferably by one angular increment. By twisting the second section in the first rotational direction, the engagement member can be disengaged from one tooth of the gear teeth, or at least locked so that the torsion application device moves the engagement member over the tooth of the gear teeth and can engage in an adjacent tooth, in particular the next adjacent tooth, through which the rotation of the coupling element relative to the sleeve in the first rotational direction is again blocked. If the second section is again twisted relative to the first section in the first rotational direction, the operation repeats. In particular, the engagement member disengages from said tooth and engages in the next adjacent tooth, and the coupling element is rotated in the first rotational direction relative to the sleeve again by one angular increment. If the locking device is a part of a metering device for an injection device, one angular increment can correspond to the desired metering step, for example the dose of 1 IU or 2 IU.

Preferably, the second section is twisted by hand, i.e., by muscular force by a user, relative to the first section in the first rotational direction, where the intermediate section becomes elastically deformed and the engagement element becomes disengaged from the tooth or the engagement becomes correspondingly locked. The torque of the torque application device and/or the elasticity of the intermediate section acting in the first rotational direction can twist the first section relative to the second section in the first rotational direction, through which the intermediate section returns to its original shape and the engagement element engages in a locking manner in the next tooth of the gear teeth.

If the torsion application device is a spring, in particular a torsion spring, it can be slackened by rotation of the coupling element in the first rotational direction and tensioned by rotation of the coupling element in the second rotational direction.

In preferred embodiments, the coupling element can be rotatable or can be rotated relative to the sleeve in the second rotational direction, which is opposite to the first rotational direction, where the engagement element of the coupling element engages via the gear teeth of the sleeve.

Alternatively, the sleeve, which can also be called the first sleeve and in whose gear teeth the engagement element of the intermediate section engages, can have an elastically disposed engagement element, which engages in gear teeth, in particular internal gear teeth, of a second sleeve surrounding the sleeve, for example a sleeve-shaped housing. The engagement element of the second sleeve can engage via the gear teeth of the first sleeve when the first sleeve is rotated in the second direction relative to the second sleeve. Rotation of the first sleeve in the second rotational direction relative to the second sleeve, which surrounds it, is preferably blocked. Thus, a one-way coupling, which allows rotation in only one rotational direction, namely the second rotational direction, is formed between the first sleeve and the second sleeve. The coupling element can be rotation-fast in the second rotational direction relative to the first sleeve. If the coupling element rotates in the second direction, the first sleeve rotates together with the coupling element, and the first sleeve is rotated in the second rotational direction relative to the second sleeve.

In preferred embodiments, the gear teeth have a plurality of teeth, where one or more, in particular each, of said teeth has a first flank pointing in a circumferential direction, and a second flank, which is opposite the first plank and points in a circumferential direction. The first flank is preferably made steeper than the second plank. Through this, a sawtooth shape of the particular tooth of the gear teeth is formed. Preferably, the engagement element presses against the first, steeper flank when the coupling element is loaded by the torque of the torque application device. The second, less steeply formed flank allows the coupling element to be rotated in the second rotational direction relative to the sleeve, so that the engagement element slides on the less steep flank and disengages from engagement with the relevant tooth.

Preferably, the engagement element is tooth-shaped, in particular sawtooth-shaped. The engagement element can have a first flank pointing in the first rotational direction and a second flank pointing in the second rotational direction, where the first flank is made steeper than the second flank. Rotation of the coupling element relative to the sleeve is prevented by the steep first flank, while the less steep second flank allows rotation of the coupling element relative to the sleeve in the second rotational direction.

Preferably, the intermediate section fits into the first section with one of its ends and into the second section with the other of its two ends. For example, the ends of the intermediate section can be chamfered. The engagement element is disposed between the two ends, preferably in the middle.

The intermediate section can be made elongated or strip-shaped, where, depending on its length, it extends over a part of the circumference of the coupling section.

In especially preferred embodiments, the intermediate section can extend from the first section in the first rotational direction and/or from the second section against the first rotational direction, i.e., in the second rotational direction. Because the intermediate section extends from the first section in the first rotational direction, a self-amplification of the locking engagement of the engagement member in the gear teeth is advantageously achieved. The self-amplifying principle is in the very broad sense comparable to a leading brake shoe of a drum brake.

In order to be able to adjust the elastic properties of the intermediate section, the intermediate section can have a smaller wall thickness than the first and/or second section of the coupling element.

In particular, the first section and/or the second section can each have an antirotation structure, through which a first and/or second rotational member can be connected rotation-fast with the relevant section. The antirotation structure can, for example, be gear teeth or a slot on the inner circumference of the first or second section. For example, the antirotation structure can form a coupling structure that is part of a separable coupling. For example, a rotational member, for example the first rotational member, can have a coupling structure that engages in the antirotation structure of, for example, the first section of the coupling element, through which the coupling is locked. The rotational member can be slidable along the lengthwise axis or axis of rotation relative to the coupling element, so that the coupling structure of the rotational member turns out from engagement with the antirotation structure, for example the first section, through which the torque application device can rotate the first rotational member relative to the coupling element, for example, in the first rotational direction.

In an advantageous further development, the second rotational member can be connected to the coupling element so that the second rotational member is pressed against a first rotation stop when it is rotated in the second rotational direction, where the first rotation stop is made on the second section and the second rotation stop is made on the first section or the intermediate section, in particular between the engagement member and the first section, or in the region where the intermediate section fits into the first section. This advantageously results in the torque acting on the second rotational member being transmitted to the first section without having to run over the entire intermediate section when the second rotational member is rotated in the second rotational direction. By bypassing the intermediate section with regard to the introduction of torque into the coupling element, the coupling element can be rotated in the second rotational direction even more easily. If the second section is twisted relative to the first section, the second rotational member, in particular a counterstop interacting with the second rotation stop, is moved away from the second rotation stop.

For example, the second rotational member can be connected to the second section of the coupling element permanently or rotation-fast in both rotational directions, in particular by means of a suitable shaft-hub connection, for example a slot that is formed on the inner circumference of the second section, in which a protrusion of the second rotational member engages. One of the sides of the slot can form the first rotation stop, where the projection of the second metering member can form the corresponding counterstop. The projection that engages in the slot, or another projection, can, for example, form the counterstop for the second rotation stop.

The first rotation stop can generally be made on the inner circumference of the second section, where the corresponding counterstop, in the rotation of the second rotational member in the first rotational direction, moves up to the first rotation stop and finally is pressed against it. Optionally, the counterstop is situated on the first rotation stop when the second rotational member is torque-loaded. The counterstop corresponding to the second rotation stop can, in the rotation of the second rotational member in the second rotational direction, be moved up to the second rotation stop and finally pressed against it. Optionally, the counterstop can be situated on the second stop, when the second rotational member is torque-loaded. As an alternative to a connection that is rotation-fast in both rotational directions, the second rotational member can be rotatable relative to the second section, in particular in a limited scale, for example small angular degrees.

Preferably, the locking arrangement is a part of drive and/or metering device for an injection device or of an injection device. The injection device serves for the administration of a liquid product, in particular a medication.

The drive and metering device comprises a winding member (second rotational member), which can be held by the user of the device, and a discharge spring, which serves as the torque application device, and which is preferably already slightly tensioned. The discharge spring preferably stores the energy needed for product discharge. The locking arrangement in accordance with the invention can be disposed, especially mechanically and/or geometrically, between the winding member and the discharge spring. The locking arrangement disposed between the winding member and the discharge spring results in one rotation of the winding member in the first rotational direction, slackening the discharge spring, and one rotation of the winding member in the second rotational direction, tensioning the discharge spring. Further, this prevents the tensioned discharge spring from slackening or the winding member from rotating backward when no external torque is applied to the winding member or the winding member is unloaded.

In preferred embodiments, a product dose that is to be administered can be adjusted with the drive and/or metering device by rotating the winding member, in particular in the first and/or second rotational direction. By rotating the winding member in the first rotational direction, the product dose to be administered can be reduced, and by rotating the winding member in the second rotational direction, the product dose can be increased. In particular, the device comprises a dose indicator member, which is coupled to the winding member so that one rotation of the winding member causes one rotation of the dose indicator member, in particular relative to a housing or an indicator device. The dose indicator member can, for example, be made sleeve-shaped, in particular as a dose indicator drum. The dose indicator member has a scale, for example helical, on its circumference, which is formed by dose values arrayed helically next to each other. With the indicator device, which is formed, for example, on the housing, the dose value that is set or to be administered can be read on the scale.

Preferably, the winding spring can be tensioned or slackened by rotating the dose indicator member.

The discharge spring can be or become linked to an advancement member, in particular a piston rod, where the discharge spring stores the energy necessary for advancement of the advancement member in the distribution direction and releases it, in particular by actuation of an actuation member. The advancement member can press on a piston of a product container, for example a cartridge, and slide the piston of the product container.

To the extent that the winding member also serves to adjust the product dose, it can also be called the metering member or the metering and winding member.

Preferably, the drive and/or metering device can have a first coupling, which is disposed, in particular mechanically, between the first rotational member or the coupling element and the discharge spring. The locked coupling can connect the first rotational member, which is disposed between the discharge spring and the coupling element, in particular the coupling element, rotation-fast with the coupling element, where the first rotational member is rotatable or not rotatable relative to the advancement member when the coupling is locked. The drive and metering device can furthermore have an actuation member that can be actuated for product discharge, in particular an actuation knob, which is disposed at the rear end of the drive and dispensing device, where the coupling is locked if the actuation member is not actuated and is open if the actuation member is actuated, or is opened by actuation of the actuation member. The actuation member can be actuated against the force of a coupling or reset spring. The coupling and/or reset spring causes the coupling to be locked when the actuation member is unactuated.

In particular, the advancement member can be connected or can be connectable, for example, to a second coupling, with the coupling member or rotational member disposed between the coupling element and the drive spring so that a rotation of the coupling or rotational member in the first rotational direction causes a movement of the drive member along the lengthwise axis in the distal direction.

In particular, the drive and/or metering device can have a second coupling, which is open if the actuation member is unactuated and is closed if the actuation member is actuated or becomes closed by actuation of the actuation member. The closed second coupling connects the coupling or rotational member and the advancement member together so that a rotation of the coupling or advancement member causes the movement of the advancement member in the distal direction.

The coupling element is preferably a part that is made of plastic, for example POM or PEEK, with or without additives such as glass, mineral or carbon fibers, in particular an injection molded part. Further, the coupling element can be made with advantageous elasticity while simultaneously having high resistance to creep by injection molding and/or by insertion and overmolding of an element, for example an insert of steel, for example spring steel or a nonferrous metal, for example bronze.

The invention was described by means of a number of preferred embodiments. In the following, preferred embodiments are described by means of drawings. The features disclosed therein form the object of the invention individually and in any combination of features, especially also advantageously with the features described above. Here:

The injection device shown in FIGS. 1-6d has a sleeve-shaped housing 4, in which a window like opening for formation of an indicator device 4a is disposed. A product container holder 5, which accommodates a product container 14 in the form of a cartridge, is affixed to the distal, i.e., the front, end of the housing 4 in a form fit, preferably inseparably, in particular snapped on. The cartridge has a cylindrical housing, in which a piston is disposed so that it can slide. At the distal end, the cartridge has a septum that can be punctured with a needle. The product that is to be administered is situated between the septum and the piston. By sliding the piston [in the] direction [of the] septum, the product is displaced from the product container 14. A threaded or bayonet connection to which the needle can be affixed is formed at the distal end of the product container holder 5. A removable cap 6 (not shown) can be placed on the product container holder 5.

Figure 1:
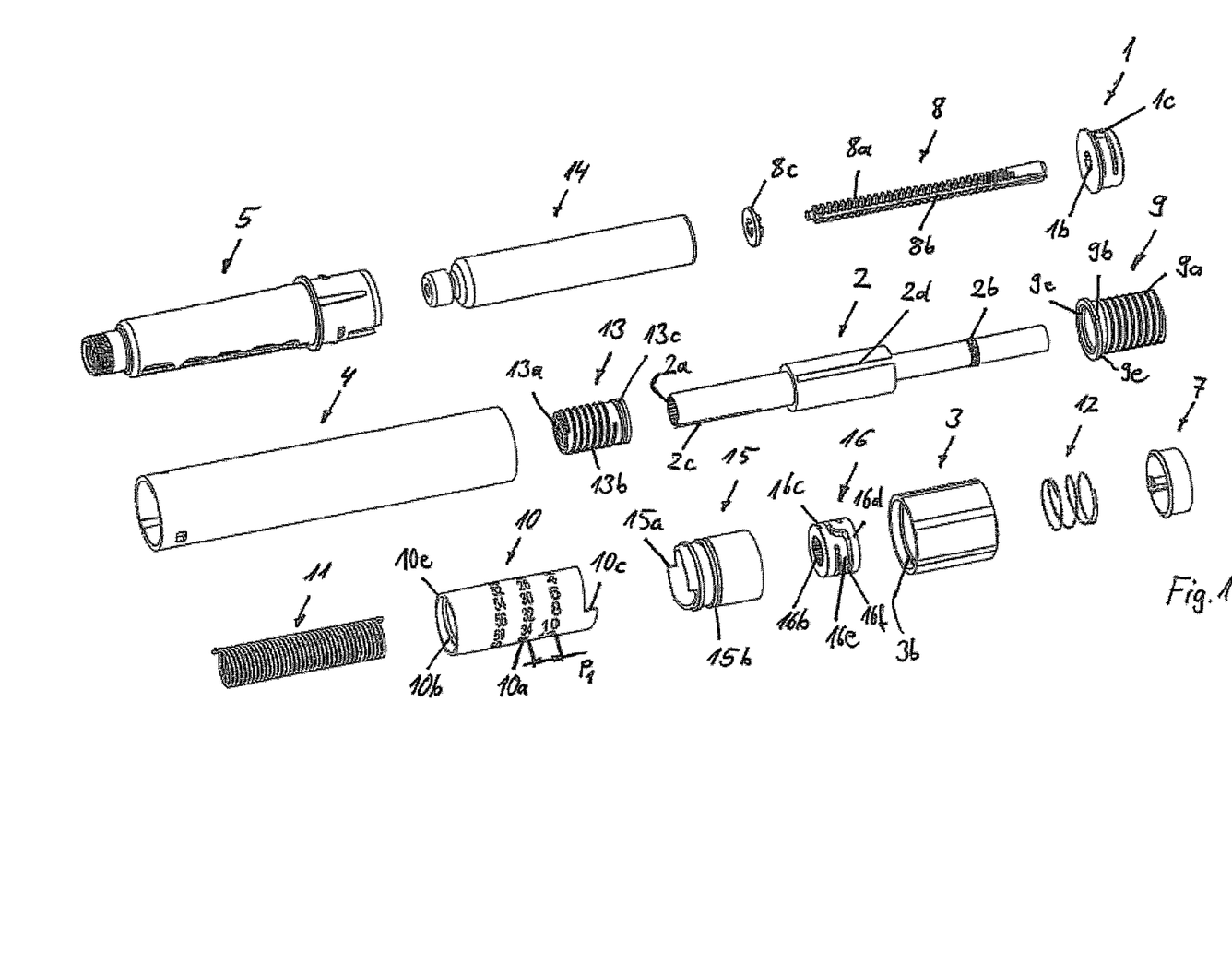
FIG. 1 shows an exploded view of the individual parts of an injection device with a locking arrangement in accordance with the invention according to a first embodiment.
Figure 2:
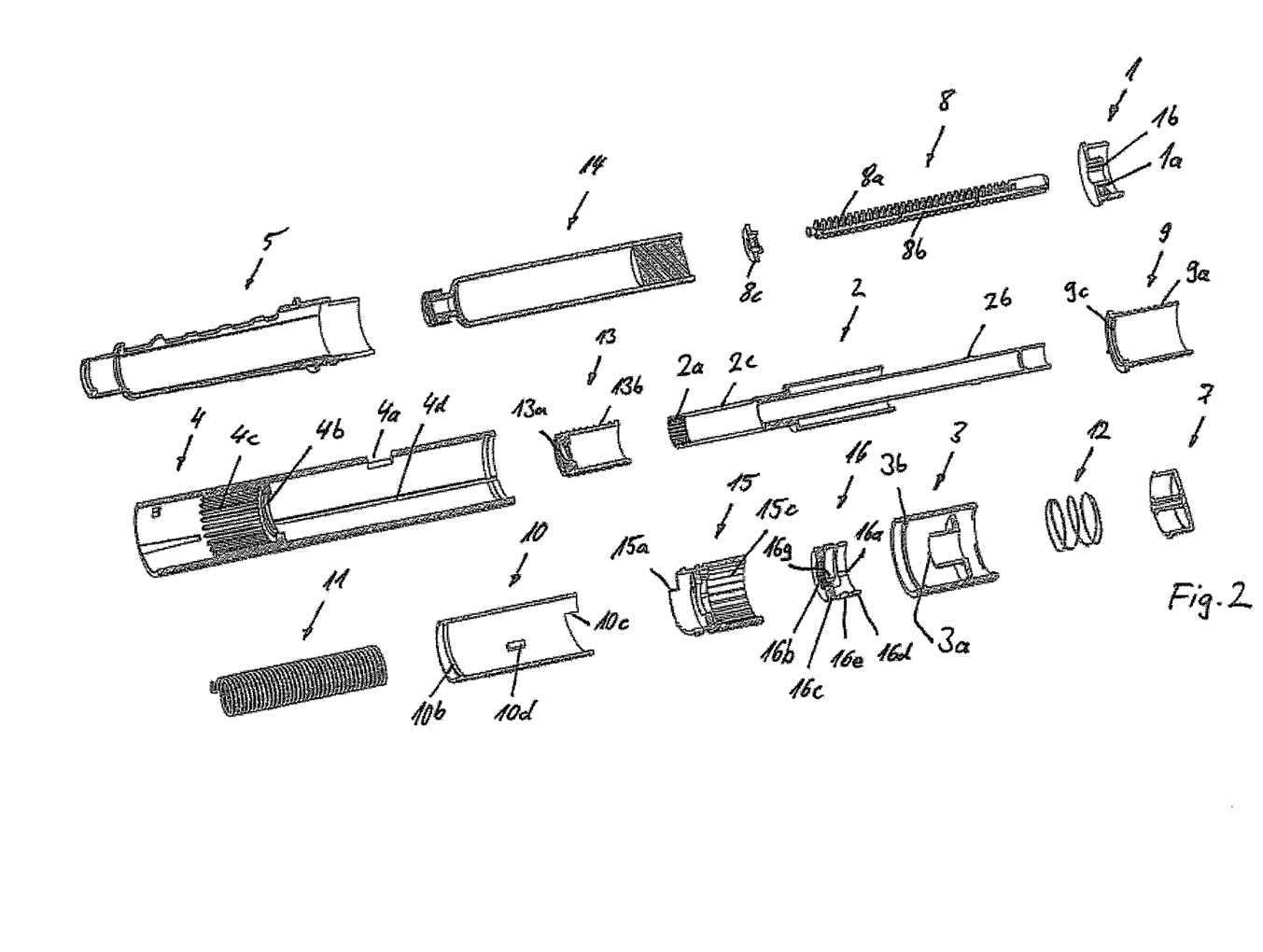
FIG. 2 shows the view from FIG. 1, where the individual parts are shown in cross section.
Figures 3A, 3B:
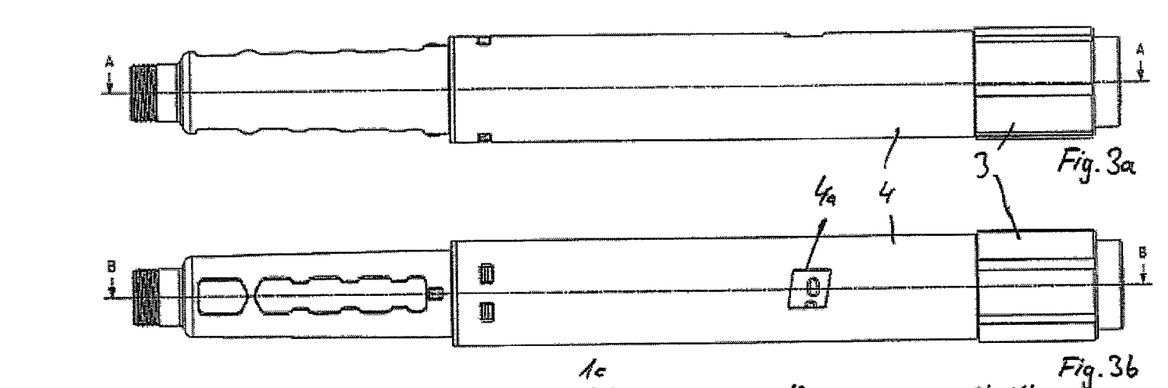
FIGS. 3a-3d show different views of an injection device composed of the individual parts of FIGS. 1 and 2 in an initial or as-delivered state.
Figure 3C:
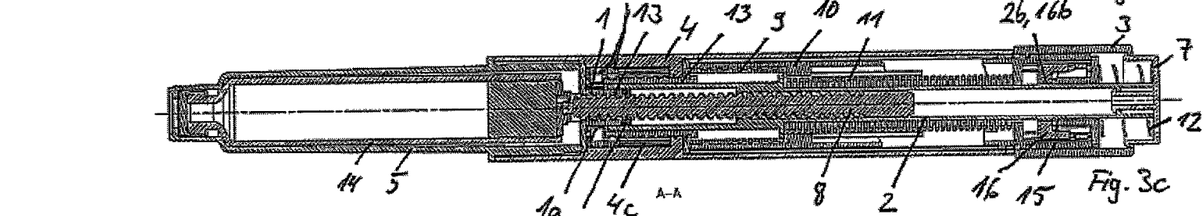
Figure 3D:
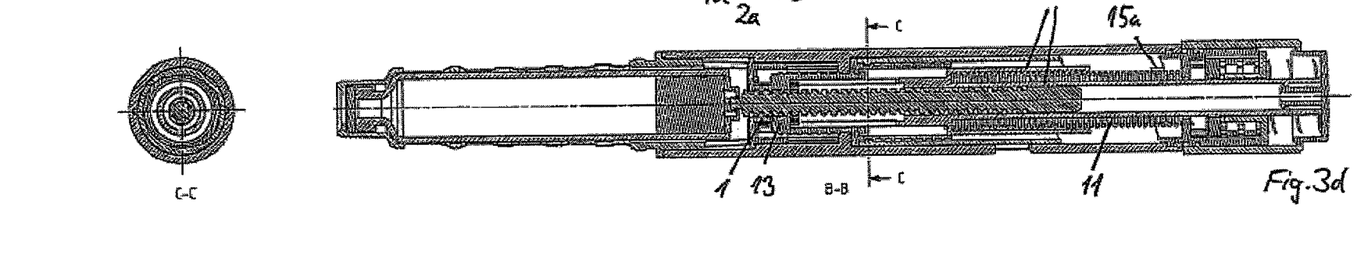
Figures 4A, 4B, 4C:
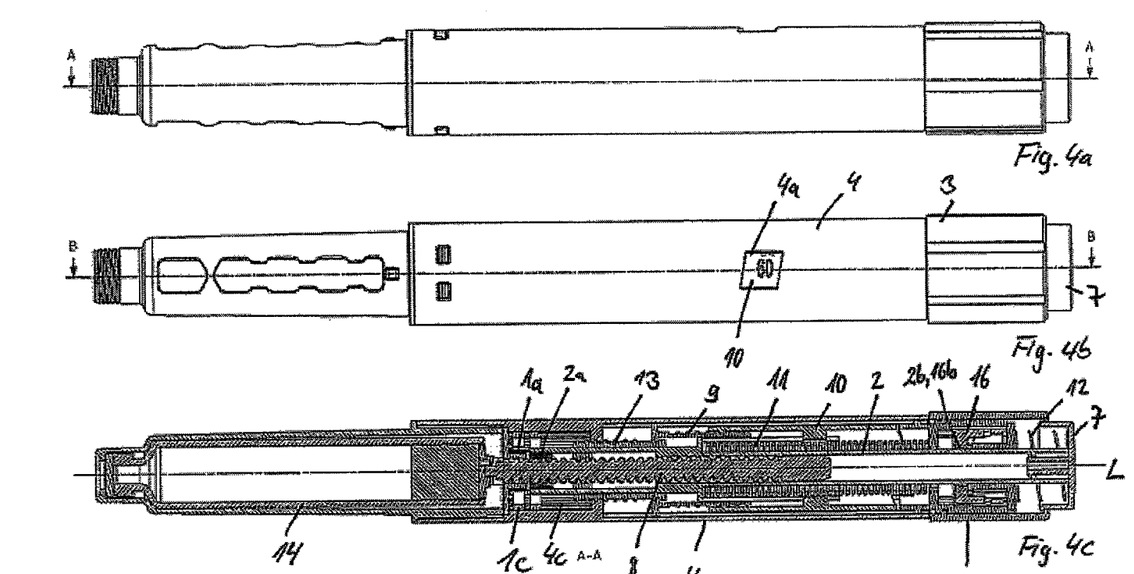
FIGS. 4a-4d show different views of the device from FIGS. 3a-3d with a maximally adjusted dose.
Figure 4D:
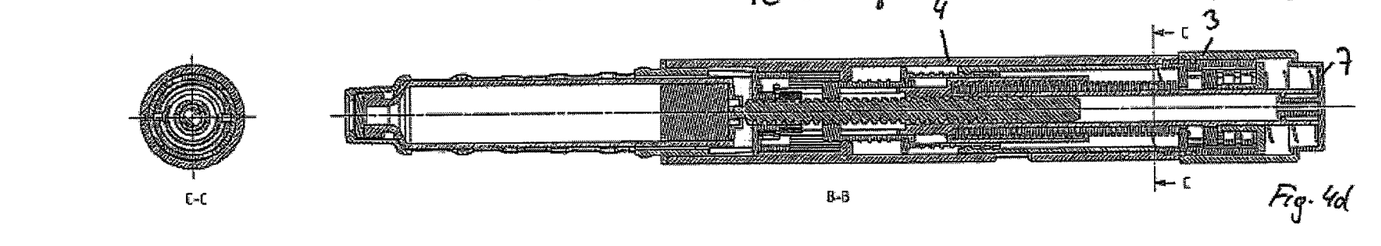

A winding member 3, which can turn relative to the housing 4 and which is called a metering member 3, is disposed at the proximal, i.e. rear, end of the housing 4. The metering member 3 forms an outer surface of the device and can be held by the user of the device and is rotatable relative to the housing 4. A rotation of the metering member 3 in a first rotational direction results in a reduction of the dose, and rotation of the metering member 3 in a second rotational direction results in an increase of the dose. The metering member 3 is connected with the housing 4 without the possibility of axial travel. A sleeve-shaped housing insert 15 is affixed rotationally and axially rigidly to the housing 4 and is thus rigidly connected with the housing and can be considered as part of the housing 4. The housing insert 15 has an annular groove 15b, in which an annular strip 3b on the inner circumference of the metering member 3 engages, through which the metering member 3 is connected rotatably and axially rigidly with the housing insert 15.

A maximum dose counterstop 15a that works in the circumferential direction for a maximum dose stop 10c of a dose indicator element 10 is formed in particular at the distal end of the housing insert 15.

Figure 7:
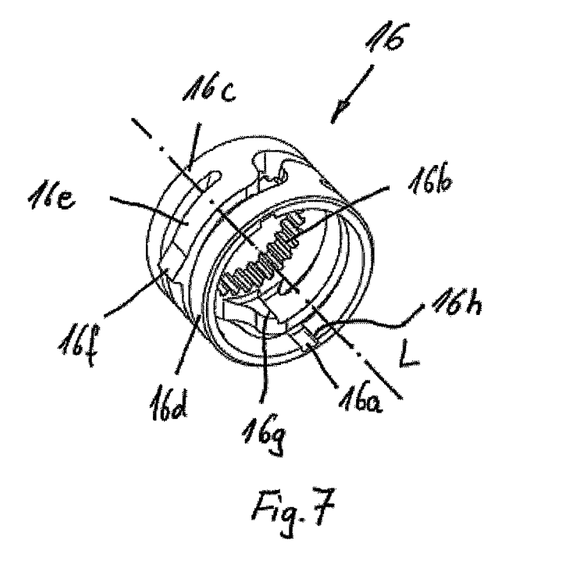
FIG. 7 shows a coupling element of the locking arrangement of the injection device as in FIGS. 1-6d and in the broader sense also for the locking arrangement as in FIG. 8.

The sleeve-shaped housing insert 15 has gear teeth 15c over its inner circumference. The housing insert 15 surrounds a one-piece coupling element 16, which is preferably made of plastic or is an injection molded part. The coupling element 16 has a first section 16c and a second section 16d, which is connected with the first section 16c via an elastically deformable intermediate section 16e. The intermediate section 16e fits at one end into the first section 16c and at the other end into the second section 16d. The intermediate section 16e extends from the first section 16c in the first rotational direction and from the second section 16d against the first rotational direction, i.e., in the second rotational direction. The intermediate section 16e is preferably elongated and extends at least over a part of the circumference of the coupling element 16. The coupling element 16 has two such intermediate sections 16e, which are offset, in particular by 180.degrees, over the circumference.

The intermediate section or sections 16e each in particular have an engagement member 16f, which engages in the gear teeth 15c of sleeve 15. The engagement member 16f is in particular formed as a tooth or lobe that projects radially outward from the circumference of the coupling element 16.

The engagement member 16f has a first tooth flank pointing in the first rotational direction and a second tooth flank pointing in the second rotational direction. The first and second tooth flanks have different steepnesses, so that the engagement member 16f is sawtooth-shaped. The first flank is preferably steeper than the second flank.

The engagement member 16f is preferably disposed between the ends of the intermediate sections 16e, preferably in the middle.

The gear teeth 15c have a plurality of teeth distributed over the circumference. One tooth or a plurality of said teeth, in particular each of said teeth can be sawtooth-shaped, for example. They can have a first flank pointing in the circumferential direction and a second flank pointing in the circumferential direction opposite the first flank, where the first flank is steeper than the second flank. Preferably, the first flank forms a counter flank for the first flank of the engagement member 16f.

A torsion spring 11, which serves as torque application device and is designed in this example as a coil spring, rests at one end, in particular the distal end, on a rotational member 2, which can be rotated relative to the housing 4, and which in this example serves as coupling member 2 and therefore is thus called, and is supported at the other end, in particular the proximal end, rigid to the housing, in particular to the housing insert 15, which can be considered to be part of the housing 4. Rotation of the coupling member 2 in the second rotational direction results in tensioning of the torsion spring 11, and rotation in the first rotational direction results in slackening of the spring 11. The coupling member 2 is preferably connected essentially rotation-fast with the metering member 3, preferably via a separable coupling 2b, 16b, in particular a first coupling. The coupling member 2 has a coupling structure 2b for formation of the first coupling. The first section 16c of the coupling element 16, for formation of the first coupling 2b, 16b, has a coupling structure 16b, which is in nonrotating engagement with the coupling structure 2b if coupling 2b, 16b is locked.

In a first variant, the metering member 3 can be connected permanently or rotation-fast in both rotational directions with the second section 16d of the coupling element 16. For the rotation-fast connection, the second section 16d has a slot 16a on its inner circumference, in which a projection 3a of the metering member 3 engages. A slot flank of the slot 16a forms a first rotational stop 16h, against which the projection 3a is pressed in a counterstop fashion, when the metering member 3 is rotated in the first rotational direction. Optionally, a stop 16g, which acts as a rotation stop and which can be called the second rotation stop, can be formed on the first section 16c or the intermediate section 16e, in particular between the engagement member 16f and the first section 16c, or at the point where the intermediate section 16e fits into the first section 16c; the stop, which can be called said second rotation stop, is pressed against a counterstop of the metering member 3, which can be formed, for example, from the rib-shaped projection 3a or another projection when the metering member 3 is rotated in the second rotational direction. Through this, the torque acting on the metering member 3 is transmitted to the first section 16c without having to run over the entire intermediate section 16e. Through this, the coupling element 16 can be rotated even more easily in the second rotational direction relative to the gear teeth 15c.

In a second variant, the metering member 3 can be connected with the second section 16d of the coupling element 16 rotation-fast in the first rotational direction and with the first section 16c or the connecting segment 16e rotation-fast in the second rotational direction. For example, the metering member 3 can thus be rotatable relative to the second section 16d, in particular on a limited scale, for example a few angular degrees. For this connection, the second section 16d has on its inner circumference the first stop 16h, at which a counterstop, in particular a projection or the longitudinal strip 3a of the metering member 3, stops in the first rotational direction. Further, the intermediate section 16e, in the region of the connection point to the first section 16c, has the second stop 16g, on which a counterstop, in particular the projection or the longitudinal strip 3a, stops in the second rotational direction.

The two variants result in the torque exerted on the coupling element 16 by the metering member 3 running over the entire connection section 16e when the metering member 3 is rotated in the second rotational direction, so that the connection section 16e can elastically deform. Further, this results in the torque exerted on the coupling element 16 by the metering member 3 being introduced onto or into the first section 16d without having to run over the entire connection segment 16e when the metering member 3 is rotated in the first rotational direction.

The torsion spring 11 supplies the first section 16c of the coupling element 16 with a torque directed in the first rotational direction about the lengthwise axis L. The magnitude of the torque is dependent on how highly the torsion spring 11 is tensioned. The engagement member 16f is pressed into the gear teeth 15c by the torque acting in the first rotational direction, so that rotation of the coupling element 16 relative to the housing insert 15 is blocked in the first rotational direction. So that engagement member 16f is reliably pressed into the gear teeth 15c, the intermediate section 16e advantageously extends from the first section 16c in the circumferential direction in the first rotational direction. As an alternative or additional measure, the first flank of the engagement member 16f and the first flank of one of the teeth of the gear teeth 15c can be matched to each other so that a self-inhibition arises between the engagement member 16f and the gear teeth 15c, i.e., even at a very high torque, the engagement member 16f is not pressed out of the gear teeth 15c. The flanks can also be matched to each other so that the engagement member 16f is pulled into engagement with the gear teeth 15c.

The second section 16d of the coupling element 16 is twistable, in particular elastically twistable, relative to the first section 16c about the lengthwise axis L in the first rotational direction, in particular by means of rotation of the metering member 3 in the first rotational direction. The twistability is provided through the elastic intermediate section 16e. Through the torsion of the second section 16d relative to the first section 16c, the engagement of the engagement member 16f in the gear teeth 15c that locks rotation in the first rotational direction is released. Through the torsion, the engagement member 16f is deflected a bit inwardly, i.e., toward the axis of rotation, so that the engagement member 16f is released from the rotation-locked engagement. Thus, rotation of the coupling element 16 relative to the housing insert 15 in the first rotational direction is enabled in this way. The engagement member 16f thus jumps over the tooth of the gear teeth 15c with which it was in rotation-locked engagement. In doing so, it is driven by the torque of the torsion spring 11 acting in the first rotational direction. The engagement member 16f engages in the next, in particular the immediately adjacent, tooth. In this way, the coupling element 16 can rotated in the first rotational direction relative to the housing insert 15 in increments or by an angular increment corresponding to the pitch of the gear teeth 15c.

Through this, the torsion spring 11 can be tensioned and slackened, and slackening of the torsion spring 11 can be prevented advantageously with a simple and cheap component, namely the sleeve-shaped coupling element 16.

By rotation of the metering member 3 in the second rotational direction, the engagement member 16f engages over the teeth of the gear teeth 15c. Spring 11 is tensioned through the locked first coupling 2b, 16b.

In order to obtain the desired elasticity of the intermediate section 16e, the intermediate section 16e can have a different wall thickness from the first and/or second section 16b, 16d, or an implementation in two-component injection molding technology overmolding of a metallic insert part, or a selected combination of these alternatives can be chosen. In the examples shown, the wall thickness of the intermediate section 16e is less than the wall thickness of the first section 16c.

An actuation member 7, which is designed as an actuation button and which can be actuated by the user of the device for product delivery, in particular can be pressed in the distal direction, is disposed at the proximal end of the drive and metering device. The actuation member 7 is disposed in reference to the dose indicator element 10 so that its position does not change during dose setting. The actuation member 7 is in particular accommodated in the metering member 3 so that it can slide by an actuation stroke. A coupling or reset spring 12 acts between the metering member 3 and the actuation member 7 and is designed as a coil spring and acts as a pressure spring. The spring 12 rests against the metering member 3 and the actuation member 7. The actuation member 7 forms the proximal end of the drive and metering device.

The actuation member 7 is connected axially rigidly with the proximal end of the coupling member 2, preferably also rotation-fast, in particular snapped on. The actuation member 7 can slide back and forth between an actuated and unactuated position against the force of spring 12, in particular by an actuation or coupling stroke.

The drive and metering device has an advancement member 8 in the form of a piston rod, at the distal end of which a flange 8c is disposed or affixed. The advancement member 8 acts on the piston of the product container 14 or preferably pushes on the piston. The advancement member 8 has an outside thread 8a, over which there is a slot 8b, which extends in the lengthwise direction of the elongated advancement element 8.

The advancement element 8 is surrounded by a rotation element 1, which is preferably sleeve-shaped and is rotationally rigid and axially slidable with respect to the advancement member 8. The advancement member 1 has a strip 1b, which engages in the slot 8b for the rotation-fast and axially slidable connection. The rotational member 1 has on its circumference a lobe-shaped engagement member 1c, disposed as a spring on a spring arm, which is engaged with an inner gear tooth 4c that is formed rigid to the housing, in particular by the housing 4.

The external thread 8a of the advancement member 8 is in a threaded engagement with an internal thread 13a of a threaded sleeve 13, so that the threaded sleeve 13 can be screwable along the length of the advancement member 8. The threaded sleeve 13 is connected to the coupling member 2 rotation-fast and axially slidable, so that the coupling member 2 rotates with the threaded housing 13. For this, an inner sleeve 13d, which is connected with the inner circumference of the threaded sleeve 13 via at least one, preferably two or more strips 13e in spoke fashion, can be made in the threaded sleeve 13. The at least one strip 13e in each case engages the coupling sleeve 2 through one, preferably two or more axially extending guide slots 2c, and in this way implements the nonrotating connection with the coupling sleeve and an axial mobility, preferably for the actuation or coupling stroke itself.

The threaded sleeve 13 is affixed to a bearing element 9 rotatably and without the possibility of axial travel. For this, the threaded sleeve 13 can, for example, have an annular slot 13c, in which the bearing element 9 engages, for example, with an annular strip 9c. The bearing element 9, for the nonrotating and slidable connection, engages with the housing 4, in particular with a projection 9b in a slot 4d of the housing 4, which extends in the lengthwise direction.

The bearing element 9 has an external thread 9a, which is engaged with an internal thread 10b of the dose indicator element 10 which is made as a dose indicator drum. In this way, the dose indicator element 10 can be screwed along the bearing element 9.

Over its circumference, the dose indicator element 10 has a coil-shaped or helical dose scale 10a that goes around it several times, which is formed from a plurality of dose values arrayed next to each other, in particular in international units (IU). The scale can have dose values that can be set, 0 to 60 or 80 IU, in single or double steps, for example. By rotating the metering member 3 relative to the housing 4 or the indicator device 4a, the desired product dose to be discharged can be set, and the corresponding dose value can be read on the indicator device 4a or appears in the indicator device 4a.

The dose indicator element 10 is in particular permanently nonrotating and axially slidable with reference to the coupling member 2. The dose indicator element 10 has on its inner circumference a projection 10d, which engages in a slot 2d that extends in the lengthwise direction of the coupling member 2.

The coupling member 2 can be connected in nonrotating fashion with the rotational member 1, in particular with a second coupling 2a, 1a. For this, the coupling member 2 has a coupling structure 2a in the form of internal gear teeth at its distal end. The coupling member 1b has a coupling structure 1a in the form of external gear teeth. If the actuation member 7 is unactuated, the second coupling 1a, 2a is open and the first coupling 2b, 16b is locked, so that the coupling member 2 can be rotated relative to the rotational member 1 and/or the advancement member 8, and the dispensing member 3, in reference to the rotational member 2, is connected to the coupling member 2 essentially rotation-fast, apart from a certain elasticity of the coupling element 16. If the actuation member 7 is in particular completely actuated, the second coupling 1a, 2a is closed, so that the coupling member 2 is rotation-fast relative to the rotational member 1 and/or to the advancement member 8, and the first coupling 2b, 16b is open, through which the coupling member 2 is rotatable relative to the metering member 3 and/or the housing 4. Between the unactuated and the completely actuated position of the actuation member 7, there is an intermediate position in which the second coupling 1a, 2a and the first coupling 2b, 16b are closed. This advantageously keeps the coupling member 2 already enabled for rotation relative to the housing 4 if the second coupling 1a, 2a is still not closed. This would in particular lead to an error function of the drive and metering device.

As soon as the first coupling 2b, 16b is open, the tension spring 11 can rotate the coupling member 2, the threaded sleeve 13, and, via the closed second coupling 1a, 2a, the rotational member 1 and the advancement member 8 relative to the housing 4, so that the advancement member 8 is shifted in the discharge direction, i.e., in the direction of the piston, and the set dose is discharged because of the relative rotation between a thread 13b on the threaded sleeve 13 and a housing thread 4b, as well as no relative rotation between the internal thread 13a and the external thread 8a of the forward feed member 8.

For dose setting, i.e., if the actuation member 7 is unactuated, the coupling member 2 is rotationally uncoupled from the advancement member 8, so that the dosing motion does not cause any discharge travel of the advancement member 8. The pitch $P_1$ of the dose scale 10a is greater than the pitch of thread 10b, 9a. So that the dose indicator element 10 moves in correspondence with the pitch $P_1$ of the dose scale 10a on a spiral or helical path, which has the same pitch as the dose scale 10a, the bearing element 9 is shifted from the threaded sleeve 13 by the difference between the pitch $P_1$ and the pitch of thread 10b. For this, the threaded sleeve 13 can have a thread 13a, 13b, which has a pitch that is equal to the difference between the pitch $P_1$ and the pitch of thread 10b. In other words, the sum of the thread 13a, 13b and thread 9a gives the pitch $P_1$ of the dose scale 10a.

The thread sleeve 13 is rotatable relative to the advancement member 8 during the setting of a dose and is not rotatable relative to the advancement member 8 during the discharge of a dose. In addition to the internal thread 13a, which meshes in the external thread 8a of the advancement member 8, the threaded sleeve 13 has the external thread 13b with the same thread pitch as thread 13a. The external thread 13b meshes in the housing thread 4b, which is formed from the housing 4. This results in the threaded sleeve 13 moving by the same distance along the lengthwise axis L relative to the housing 4 during the setting of a dose as it moves relative to the advancement member 8. Because of the two threads 13a, 13b, the advancement member 8 does not need to be in engagement with the housing 4.

Relative to FIGS. 3a-d, the drive and metering device, which together with the product container 14 and product container holder 5 forms an injection device, is shown in a starting position or in an as-delivered condition, where the dose is set to zero. The actuation member 7 is unactuated, and spring 12 presses the actuation member 7 in the proximal direction, so that the first coupling 2b, 16b is closed and the second coupling 1a, 2a is open. The torsion spring 11, which acts as discharge spring, is preferably tensioned in the delivered state.

By rotation of the metering member 3 in the second rotational direction, the coupling member 2 is rotated relative to the housing 4 over the closed first coupling 2b, 16b, so that the threaded sleeve 13 with its external thread 13b on housing 4 and with its internal thread 13a on the advancement member 8 is screwed along, in particular in the proximal direction, so that it carries the bearing element 9 in the axial direction and shifts the bearing element 9 in a nonrotating manner along the housing 4 in the proximal direction. Because of the rotation of coupling member 2, the dose indicator element 10 is also rotated and screwed along on the bearing element 9 by its thread 10b. The screwing motion of the dose indicator element 10 relative to the bearing element 9 is overlapped by the axial motion of the bearing element 9 relative to the housing 4, through which the dose indicator element 10 describes a spiral or helical path with regard to the housing 4, the path corresponding to the pitch $P_1$ of dose scale 10a. As the dose is increased, the maximum dose stop 10c moves toward the maximum dose counterstop 15a. If the maximum dose that can be set is reached with the drive and metering device, here 60 IU as an example, the maximum dose stop 10c hits the maximum dose counterstop 15a (FIGS. 4a-d). By rotating the metering member 3 in the first rotational direction, the set dose can be corrected or reduced, and the maximum dose stop 10c moves away from the maximum dose counterstop 15a, and a zero dose stop 10e, which is formed by the rear side of the dose indicator element 10 and acts as an axial stop, moves toward a zero dose counterstop 9e, which is formed by a collar of the bearing element 9.

When the metering member 3 is rotated in the first rotational direction, the spring 11 is slackened, and it is tensioned upon rotation in the second rotational direction. If the user lets go of the metering member 3, the coupling element 16 keeps the spring 11 from slackening.

To discharge the set dose, the actuation member 7 is shifted in the distal direction against the force of spring 12, through which the second coupling 1a, 2a becomes closed and the first coupling 2b, 16b is opened. Spring 11 now drives the coupling member 2 rotationally in the second rotational direction, and the advancement member 8 remains fixed relative to the threaded housing 13 and is screwed in the distal direction together with the thread housing 13 by means of thread 13b and thread 4b on the housing 4, and thus shifts the piston into the product container 14. Here, the engagement member 1c moves over the gear teeth 4c, through which the discharge of the product dose is signaled by means of clicking sounds. The engagement member 1c with gear teeth 4c also forms a unidirectional coupling that results in the rotational member 1 being rotatable in only one direction, namely in the first rotational direction, which shows results in products discharged.

Figure 5A:
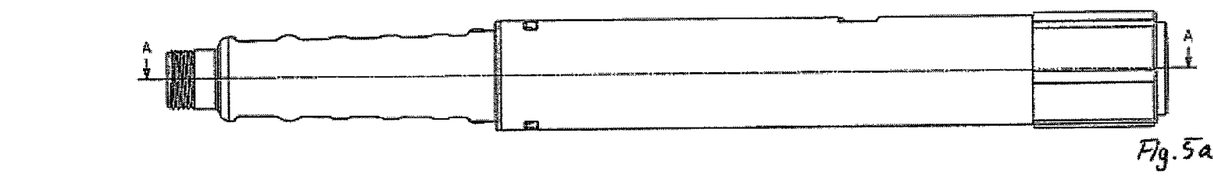
FIGS. 5-5d show different views of the device from FIGS. 3a-3d after delivery of the set product dose.
Figures 5B, 5C, 5D:
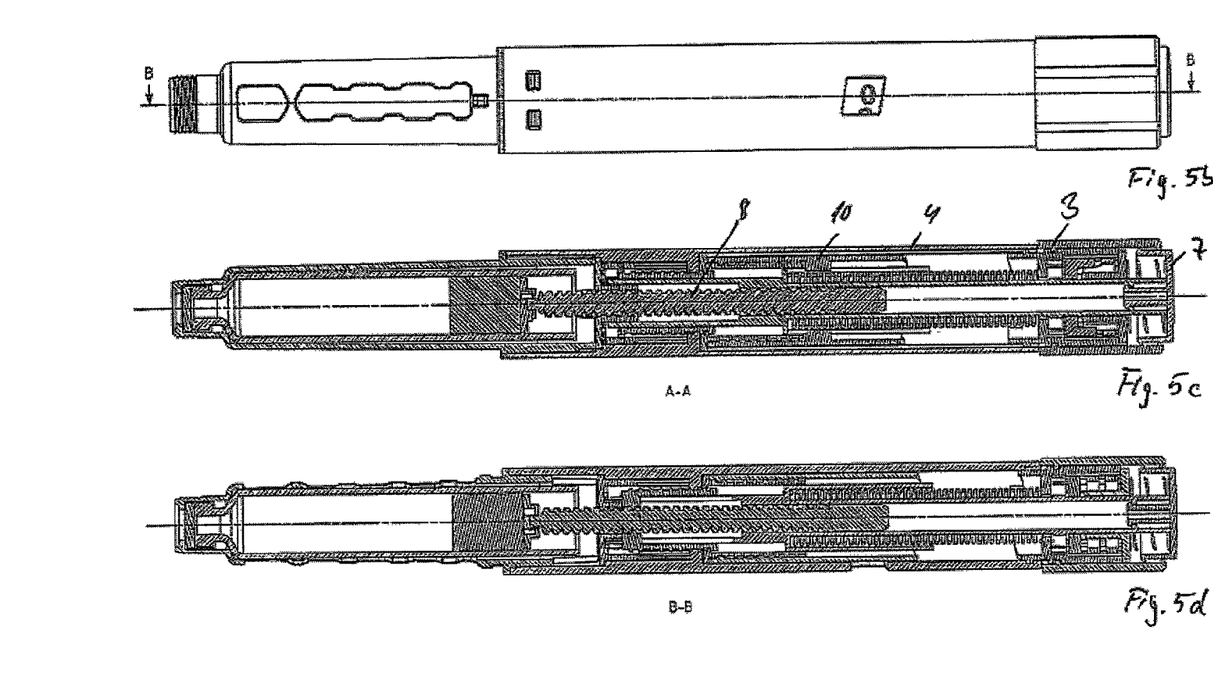
Figure 6A:
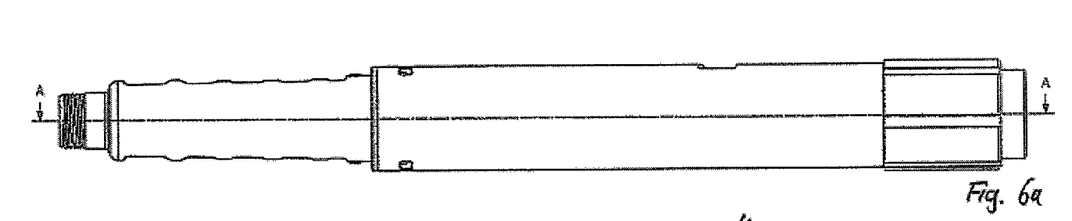
FIGS. 6a-6d show different views of the device from FIGS. 3a-3d in a state in which the product dose contained in the product container is less than the maximum dose that can be set with the device.
Figure 6B:
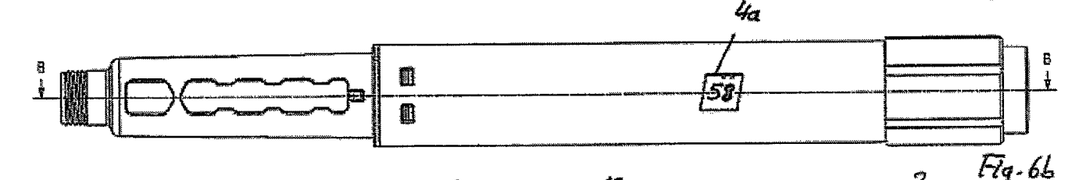
Figure 6C:
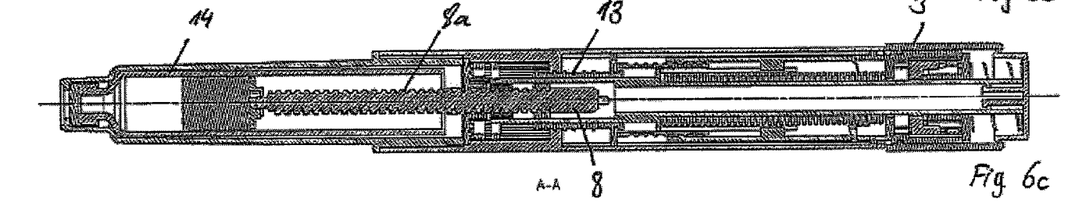
Figure 6D:
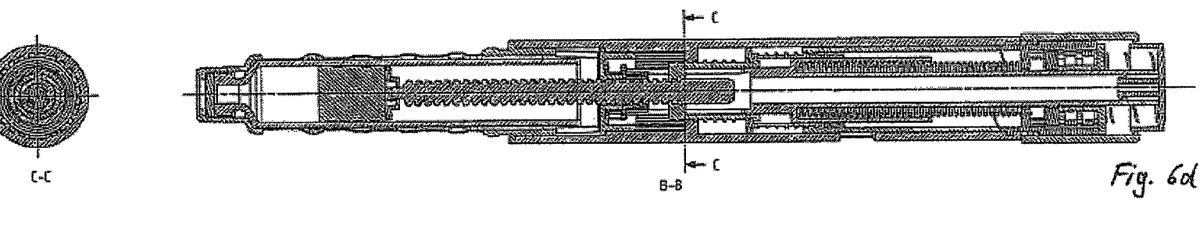

Through the rotational motion of the coupling member 2 in the first rotational direction, the dose indicator element 10 is screwed back on the bearing element 9, in particular, the zero dose stop 10e moves in the direction of the zero dose counterstop 9e, so that the dose scale 10a in the indicator element 4 counts backward to the zero dose. When the dose "zero" is shown in the indicator device 4a (FIGS. 5a-d) or the zero dose stop 10e hits the zero dose counterstop 9e, the discharge is complete. In FIGS. 5a and 5b, the drive and metering device is shown at the end of the product discharge, where the actuation member 7 is still actuated, i.e., has not been released by the user of the device.

Through repeated metering and actuation of the actuation member 7, the product contained in the product container 14 can be discharged in a plurality of selectable individual doses. Also, a discharge can be interrupted or restarted by releasing or again actuating the actuation member.

In FIGS. 6a-d, the drive and metering device is shown in a state in which a dischargeable dose of the product that is less than the maximum dose that can be set with the drive and metering device is contained in the product container 14. In the example shown, only 58 IU are still contained in the product container 14, where a maximum of 60 IU could be set with the drive and metering device. In order to avoid misuse, the drive and metering device comprises a limiting arrangement that limits the dose setting. For this, the advancement element 8 has a stop at the proximal end of thread 8a at which the threaded sleeve 13 stops, so that one rotation of the metering member 2 in the second rotational direction is blocked even if the maximum dose stop 10c is not in the stop position with the maximum dose counterstop 15a. However, rotation of the metering member 3 in the first rotational direction is possible.

Figure 8:
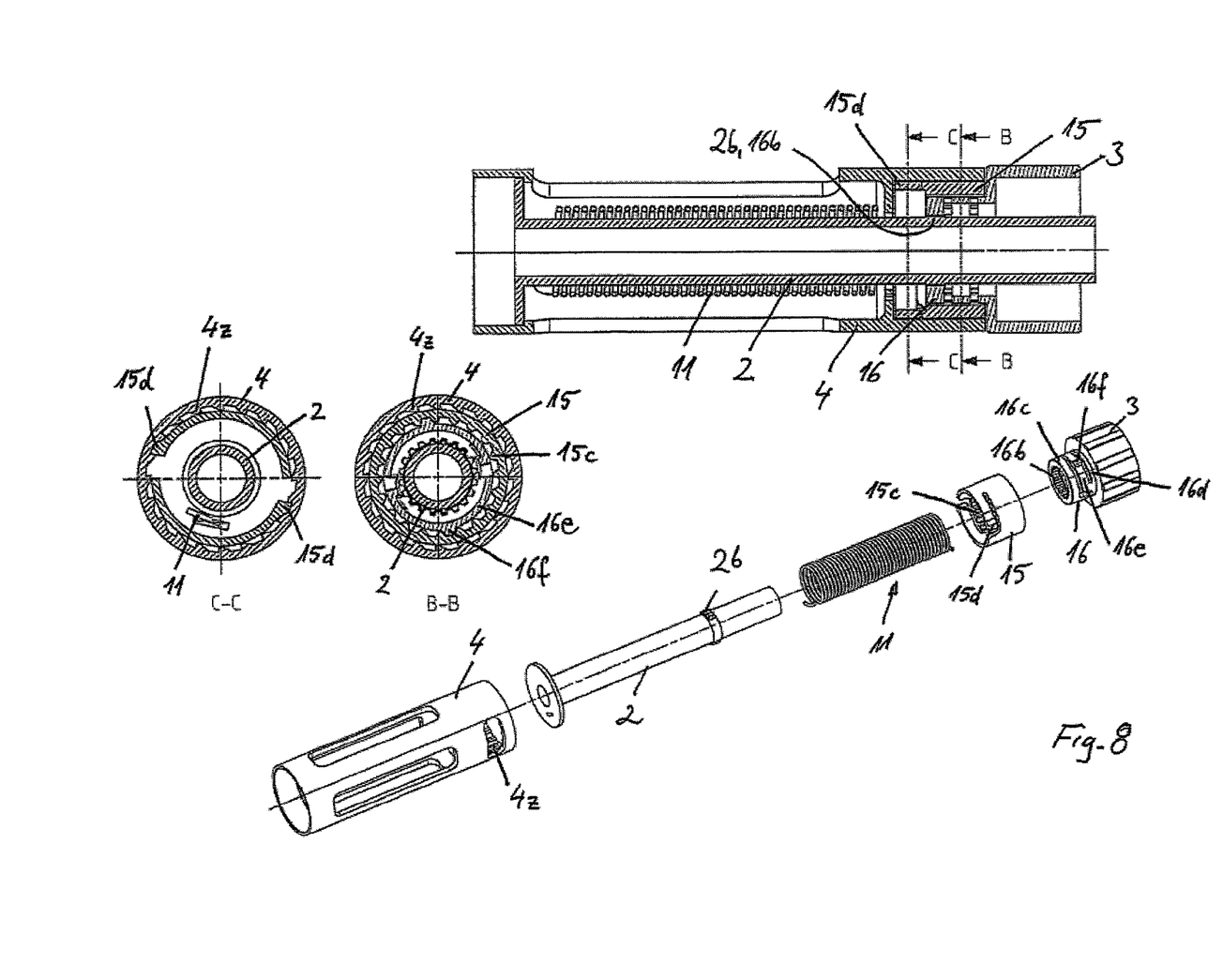
FIG. 8 shows different views of a second embodiment of a locking arrangement.

FIG. 8 shows a locking arrangement, whose coupling element 16 is very similar to the device from FIGS. 1-6d and differs primarily by the shape of the engagement member 4f and by the fact that the winding member 3 is made integral, i.e., as a unit, on a second section of the coupling element 16. In particular with regard to the design of the coupling element 16 and the function of separating the engagement element 4f from engagement with gear teeth 15c, one is referred to the description for FIGS. 1-7.

The locking arrangement from FIG. 8 comprises a coupling element 16 disposed between the winding member 3 and the rotational member 2. By rotation of the winding member 3 relative to a sleeve-shaped housing 4 in a first direction, the spiral spring 11, which acts as a torsion spring, can be slackened, and by rotation in a second rotational direction opposite to the first, it can be tensioned.

Slackening of spring 11 is prevented in particular by the coupling element 16, when the winding element 3 is unloaded, i.e., free from external torques, as applied, for example by the user.

The engagement member 16f has a first tooth flank pointing in the first rotational direction and a second tooth flank pointing in the second rotational direction. The first and second tooth flanks in the example shown have approximately the same steepness, so that the engagement member 16f is trapezoidal in shape.

The gear teeth 15c have a plurality of teeth distributed over the circumference. One tooth or a plurality of said teeth, in particular each of said teeth, can be made sawtooth or trapezoidal in shape. They can have a first flank pointing in the circumferential direction and a second flank pointing in the circumferential direction opposite the first flank, where the first flank is made steeper than the second flank or has approximately the same steepness as the second flank. The first flank forms a mating flank for the first flank of the engagement member 16f.

The engagement between the engagement member 16f and the gear teeth is such that the coupling element 16 is not rotatable in the second rotational direction with reference to sleeve 15, i.e., it is rotation-fast.

Spring 11 rests at one end, in particular the distal end, against a rotational member 2 that can rotate relative to housing 4, and at the other end, in particular the proximal end, rigidly on the housing, in particular on the housing insert 15. A rotation of the rotational member 2 in the second rotational direction results in tensioning of the torsion spring 11, where rotation in the first rotational direction causes slackening of spring 11. The rotational member 2 is preferably connected to the winding member 3 via a separable coupling 2b, 16b in an essentially nonrotating manner. The coupling member 2, for formation of coupling 2b, 16b, has a coupling structure 2b. The first section 16c of the coupling element 16, for formation of the second coupling 2b, 16b, has a coupling structure 16b, which is in a nonrotating engagement with the coupling structure 2b when coupling 2b, 16b is closed.

The winding member 3 is made in one piece with the second section 16d of the coupling element 16, for example as an injection molded part made of plastic.

The gear teeth 15c are made on the inner circumference of a first sleeve 15, in particular a ratchet sleeve, which is rotatable only in the second rotational direction relative to housing 4 and is not rotatable in the first rotational direction. The first sleeve 15 has a springy engagement member 15d, which is in engagement with gear teeth 4z of a second sleeve, which is formed from the sleeve-shaped housing 4, so that the first sleeve 15 is rotatable in the second rotational direction and is not rotatable in the first rotational direction. This arrangement can also be called a ratchet. The teeth of the gear teeth 4z are sawtooth-shaped, i.e., they have one flank that is less steep and one that is more steep, and the preferably sawtooth-shaped engagement member 15d can slide over the less steep flank and stop against the steeper flank.

Rotation of the winding member 3 and/or the coupling element 16 in the second rotational direction results in the first sleeve 15 rotating together with coupling element 16, where the engagement member 15d of sleeve 15 engages via the gear teeth 4z of housing 4. The spring 11 is tensioned by rotation in the second rotational direction.

The rotational member 2 can be axially shifted relative to the coupling element 16, so that the first coupling 2b, 16b connects, in closed state, the second section of the coupling element 16 in a nonrotating fashion with the rotational member 2, and becomes open so that the rotational member 2 is rotatable in the first rotational direction relative to the coupling element 16, so that the spring 11 can transmit the spring energy stored in it to the rotational member 2.

A piston rod, for example, of an injection device, can be coupled to the rotational member 2, in particular via second coupling (FIGS. 1-6d) so that the rotation of the rotational member 2 results in an advancing movement of the piston rod. Through this, a product can be discharged from a product container.

REFERENCE LIST

1 Rotational member
1a Second coupling structure
1b Strip
1c Engagement member/cam
2 Coupling member/first rotational member
2a First coupling structure/internal gear teeth
2b Third coupling structure
2c Guide slot
2d Guide/lengthwise guide/slot
3 Metering member/winding member/second rotational member
3a Projection/longitudinal strip
3b Annular strip
4 Housing
4a Indicator device
4b Thread/internal thread
4c Gear teeth/internal gear teeth
4d Lengthwise guide/slot
4e Internal thread
4f Engagement member
4z Gear teeth
5 Product container
6 Cap (not shown)
7 Actuation member/actuation knob
8 Advancement member/ram/piston rod
8a External thread
8b Lengthwise guide/slot
8c Flange
9 Bearing element
9a Thread/external thread
9b Projection
9c Annular strip
9e Zero dose counterstop
10 Dose indicator element
10a Dose scale
10b Thread/internal thread
10c Maximum dose stop
10d Engagement cam/projection
10e Zero dose stop
11 Spring/discharge spring/torsion spring
12 Coupling spring/reset spring
13 Threaded sleeve
13a Internal thread/thread
13b External thread/thread
13c Annular slot
13d Internal sleeve
13e Strip
14 Product container
15 Housing insert/first sleeve/ratchet sleeve
15a Maximum dose counterstop
15b Annular slot
15c Internal gear teeth/gear teeth
15d Engagement member
16 Coupling element/two-way coupling
16a Stop/edge/slot
16b Antirotation device/fourth coupling structure
16c First section
16d Second section
16e Intermediate section
16f Engagement member/first tooth flank/second tooth flank
16g Second stop/edge
16h First stop/slot flank
L Lengthwise axis/axis of rotation
$P_1$ Pitch of dose scale

The invention claimed is:

1. A locking arrangement for a medicinal drug administration device comprising:
    a) a sleeve with gear teeth on its inner circumference,
    b) a sleeve-shaped, one-piece coupling element comprising a longitudinal axis (L) surrounded over its circumference by the sleeve and having a first section and a second section, wherein the first section is connected with the second section via an elastically deformable intermediate section, the intermediate section comprising an engagement member for engaging the gear teeth on the inner circumference of the sleeve; and
    c) a torque application means for applying a torque in a first rotational direction about the longitudinal axis (L) to the first section of the coupling element, whereby the engagement member is releasably pushed by the torque into the gear teeth on the inner circumference, such that rotation of the coupling element relative to the sleeve is blocked in the first rotational direction, d) wherein said second section of the coupling element is twistable about the longitudinal axis (L) relative to the first section in the first rotational direction, resulting in elastic deformation of the intermediate section, whereby blocking in the first rotational direction by releasable engagement of the engaging member in the gear teeth on the inner circumference is released, such that rotation of the coupling element relative to the sleeve in the first rotational direction is enabled.

2. The locking device of claim 1 wherein the torque application means is a rotary or helical spring and the first section and second section of the coupling are each ring-shaped and spaced from each other along longitudinal axis (L) by the intermediate section.

3. The locking arrangement as in claim 1, wherein the coupling element is rotatable relative to the sleeve in a second rotational direction opposite to the first rotational direction, wherein the engagement member engages over the gear teeth.

4. The locking arrangement as in claim 1, wherein the coupling element is nonrotational relative to the sleeve in a second rotational direction that is opposite to the first rotational direction, and wherein the sleeve has an additional elastically disposed engagement member, which engages in gear teeth of a housing sleeve surrounding the sleeve and the additional engagement member engages the housing sleeve surrounding the sleeve via the gear teeth of the housing sleeve, so that the coupling element can be rotated in the second rotational direction.

5. The locking arrangement as in claim 4, wherein the gear teeth of the sleeve and housing sleeve comprise a plurality of teeth, where one or more of said teeth comprises a first flank pointing in a circumferential direction and a second flank pointing in a circumferential direction opposite to the first flank, wherein the first flank is made steeper than the second flank.

6. The locking arrangement as in claim 1, wherein the engagement member of the coupling element is tooth-shaped, and wherein said engagement member comprises a first flank pointing in the first rotational direction and a second flank pointing in the second rotational direction, wherein the first flank is made steeper than the second flank.

7. The locking arrangement as in claim 1, wherein the intermediate section fits at one end into the first section and at the other end into the second section, wherein the engagement member is disposed between the two ends.

8. The locking arrangement as in claim 1, wherein the intermediate section extends from the first section in the first rotational direction and/or extends from the second section opposite to the first rotational direction.

9. The locking arrangement as in claim 1, further comprising a second rotational member that is connected to the coupling element so that it is pressed against a first rotational stop of the coupling element when it rotates in the first rotational direction, and is pressed against a second rotational stop acting in the opposite rotational direction when it is rotated in the second rotational direction, where the first rotational stop is made on the second section and the second rotational stop is made on the first section or the intermediate section.

10. The locking arrangement as in claim 1, wherein the first section and/or the second section has an antirotation structure.

11. A medicinal drug administration device comprising:
a locking arrangement for controlling action of the device, comprising:

a) a sleeve with gear teeth on its inner circumference, b) a sleeve-shaped, one-piece coupling element comprising a longitudinal axis (L) surrounded over its circumference by the sleeve and having a first section and a second section, wherein the first section is connected with the second section via an elastically deformable intermediate section, the intermediate section comprising an engagement member for engaging the gear teeth on the inner circumference of the sleeve; and c) a torque application means for applying a torque in a first rotational direction about the longitudinal axis (L) to the first section of the coupling element, whereby the engagement member is releasably pushed by the torque into the gear teeth on the inner circumference, such that rotation of the coupling element relative to the sleeve is blocked in the first rotational direction, d) wherein said second section of the coupling element is twistable about the longitudinal axis (L) relative to the first section in the first rotational direction, resulting in elastic deformation of the intermediate section, whereby blocking in the first rotational direction by releasable engagement of the engaging member in the gear teeth on the inner circumference is released, such that rotation of the coupling element relative to the sleeve in the first rotational direction is enabled, and further comprising a drive and/or dosing device to aid administration of a liquid medication, comprising:

a second rotational member that can be gripped by the user of the administration device and wherein the torque application means is a spring that can be tensioned by rotation of the second rotational member, wherein the spring stores the energy needed to discharge the medication, and the locking arrangement is disposed between the second rotational member and the spring.

12. The medicinal drug administration device of claim 11 wherein a medication dose to be administered can be set with the drive and/or dosing device by rotating the second rotational member, and further comprising a dose indicator element coupled to the second rotational member so that one rotation of the second rotational member results in one rotation of the dose indicator element.

13. The medicinal drug administration device of claim 11 further comprising a first coupling, which is disposed between the coupling element and the spring storing discharge energy, and an actuation member that can be actuated for medication discharge, wherein the first coupling is closed if the actuation member is unactuated and is opened if the actuation member is actuated or is opened by actuation of the actuation member.

14. The medicinal drug administration device of claim 13 wherein the first coupling when closed connects a first rotational member, in particular a coupling member, that is disposed between the spring storing discharge energy and the coupling element rotation-fast with the coupling element, wherein the first rotational member, if the first coupling is closed, can be rotated relative to an advancement member that acts on a piston of a medication container.

15. The medicinal drug administration device of claim 11 further comprising an elongated advancement member, whose distal end can act on a piston of a medication container, and the shift of which in a distal direction results in the piston in the medication container being shifted, where the advancement member is connected or is connectable with a first rotational member disposed between the coupling element and the spring storing discharge energy so that a rotation of the first rotational member results in a movement of the advancement member in the distal direction.

16. The medicinal drug administration device of claim 15 further comprising an actuation member that can be actuated for the medication discharge and a second coupling, which is open if the actuation member is unactuated and is closed if the actuation member is actuated or is closed by actuation of the actuation member, wherein the second coupling when closed connects the first rotational member and the advancement member to each other so that a rotation of the first rotational member results in the movement of the advancement member in the distal direction.

17. A locking arrangement for a medicinal drug administration device comprising:
   a) a sleeve with gear teeth over an inner circumference,
   b) a sleeve-shaped, coupling element with a longitudinal axis (L), which is surrounded over its circumference by the sleeve and which has a first section and a second section, wherein the first section is interconnected with the second section via an elastically deformable intermediate section, having an engagement member that engages the gear teeth of the sleeve; and
   c) wherein the locking arrangement is adapted to press the engagement member into the gear teeth upon reception, by the first section, of a torque directed about the lengthwise axis (L) in a first rotational direction, so that rotation of the coupling element relative to the sleeve is blocked in the first rotational direction, and
   d) wherein the second section of the coupling element can be twisted relative to the first section about the lengthwise axis (L) in the first rotational direction, resulting in elastic deformation of the intermediate section, so that the engagement of the engagement member in the gear teeth locking the rotation in the first rotational direction can be released, so that the coupling element becomes free to rotate in the first rotational direction relative to the sleeve.

18. The locking arrangement as in claim 17, further comprising a rotational member that is connected to the coupling element so that it is pressed against a first rotational stop of the coupling element when it rotates in the first rotational direction, and is pressed against a second rotational stop acting in the opposite rotational direction when it is rotated in the second rotational direction, where the first rotational stop is made on the second section and the second rotational stop is made on the first section or the intermediate section.

19. The locking arrangement as in claim 18, wherein the coupling element is rotatable relative to the sleeve in a second rotational direction opposite to the first rotational direction, wherein the engagement member engages over the gear teeth.

20. The locking arrangement as in claim 17, further comprising a second rotational member that can be gripped by the user of the device and a torque application means that is a spring that can be tensioned by rotation of the second rotational member, wherein the spring stores the energy needed to discharge the medication, and the locking arrangement is disposed between the second rotational member and the spring.

* * * * *